United States Patent [19]

Okamura et al.

[11] 3,955,012

[45] May 4, 1976

[54] METHOD FOR MANUFACTURING MEDICAL ARTICLES COMPOSED OF SILICONE RUBBER COATED WITH COLLAGEN

[75] Inventors: Seizo Okamura, Kyoto; Tsunetoshi Hino, Higashi-Osaka, both of Japan

[73] Assignee: Zaidan Hojin, Seisan Kaihatsu Kagaku Kenkyusho, Kyoto, Japan

[22] Filed: Nov. 16, 1973

[21] Appl. No.: 416,658

Related U.S. Application Data

[63] Continuation-in-part of Ser. No. 167,850, July 30, 1971, Pat. No. 3,808,113.

[30] Foreign Application Priority Data

Aug. 6, 1970  Japan .................. 45-68898

[52] U.S. Cl. ........................... 427/2; 3/1; 128/DIG. 8; 128/DIG. 21; 204/159.12; 204/159.13; 424/31; 424/36; 427/37; 427/44; 427/54; 427/353
[51] Int. Cl.² ........................... B05D 3/06
[58] Field of Search ..... 117/47 A, 93.1 R, 93.1 CD, 117/93.31, 138.8 B, 138.8 A, 164; 204/159.12, 159.13; 3/1, DIG. 1; 128/214 D, DIG. 8, DIG. 21; 424/31, 36; 427/2, 44, 54

[56] References Cited

UNITED STATES PATENTS

| | | | |
|---|---|---|---|
| 3,188,229 | 6/1965 | Graham | 117/93.31 |
| 3,451,394 | 6/1969 | Bechtol et al. | 117/93.31 |
| 3,632,386 | 1/1972 | Hurst | 117/93.1 CD |
| 3,649,347 | 3/1972 | Battista | 117/164 |

FOREIGN PATENTS OR APPLICATIONS

| | | | |
|---|---|---|---|
| 751,991 | 7/1956 | United Kingdom | 117/93.1 CD |
| 900,181 | 7/1962 | United Kingdom | 117/93.1 CD |

*Primary Examiner*—J. H. Newsome
*Attorney, Agent, or Firm*—Stevens, Davis, Miller & Mosher

[57] ABSTRACT

Medical articles composed of silicone rubber coated with collagen to be used in living body, are manufactured by subjecting a surface of shaped articles composed of silicone rubber to a spark discharge, coating the thus treated surface with an acidic aqueous solution of collagen and then drying said surface to form collagen layer and irradiating the shaped article coated with collagen with high energy ionizing radiation under an atmosphere having such a humidity that the water content of the coated collagen becomes more than 20% by weight.

5 Claims, 7 Drawing Figures

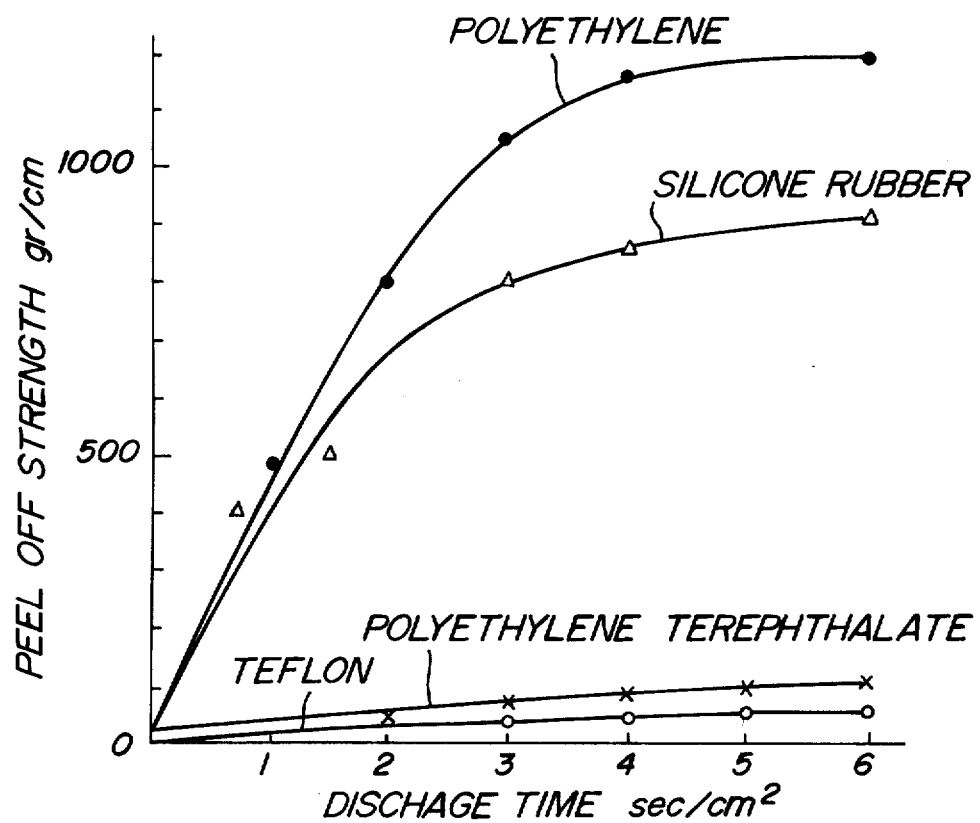
FIG_7

METHOD FOR MANUFACTURING MEDICAL ARTICLES COMPOSED OF SILICONE RUBBER COATED WITH COLLAGEN

This application is a continuation-in-part of our application Ser. No. 167,850, filed on July 30, 1971 now U.S. Pat. No. 3,808,113.

The present invention relates to a method for manufacturing medical articles composed of silicone rubber coated with collagen, which are used in direct contact with a living body.

The object of the present invention is to provide a novel method for manufacturing medical articles composed of silicone rubber coated with collagen strongly which can satisfy the following requirements for the medical articles to be used in a living body, that is 1: no toxicity and carcinogenic property
2: no antigenic-antibodic property
3: no coagulation of blood
4: affinity to the living body Recently, synthetic high polymeric materials have been used in medical field and particularly various synthetic high polymers, such as polyethylene, polypropylene, polyethylene terephthalate, Teflon (trademark of polytetrafluoroethylene made by E. I. du Pont de Nemours & Co. Inc.), silicone rubber and the like have been used to form artificial blood vessels, artificial organs, blood ducts, and blood container. However, the medical articles to be used in a living body, which are manufactured from the above described various synthetic high polymers, cannot satisfy the above described requirements fully.

The term "silicone rubber" used herein means organo-silicone rubber mainly consisting of dimethyl polysiloxane, which is, for example, referred to as Phycon in trademark made by a joint venture of Dow Corning Co. and Fuji Kobunshi Kogyo K.K. and is limited to a medical grade.

It has been said that polyethylene, polyethylene terephthalate, Teflon, silicone rubber, etc. among the various synthetic high polymers have relatively favorable properties as the materials for medical articles to be used in a living body and among them silicone rubber has a resistance to coagulation of blood and suits for medical articles to be used in a living body and for example, a surface treating agent composed of liquid silicone which is used as a coating agent for medical articles, is commercially available but it is not complete and when using in a living body an agent for preventing coagulation of blood having a high activity, such as heparin should be used together.

It has been proposed to use collagen, which is one kind of high polymers constituting a living body, as a material for medical article to be used in a living body. Collagen is obtained in a water soluble form and such a process is disclosed in U.S. Pat. No. 3,034,852 and U.S. Pat. No. 3,530,037. Collagen has a compatibility to the living body and the purified collagen in which telopeptide in the end of molecule is removed by an enzyme treatment has no antigenecity and has a high affinity to heparin, so that the collagen is suitable for material of medical articles to be used in a living body.

However, the above described collagen is insufficient in the mechanical strength and elasticity and it is difficult to use collagen as a single material for producing the above described medical articles, such as artificial blood vessels and artificial organs.

The inventors have studied the materials for producing said medical articles in view of the synthetic high polymers and high polymers constituting the living body and noticed that if the medical articles composed of synthetic high polymers, the surface of which is coated tightly with collagen, can be manufactured, such medical articles can satisfy all the above described four requirements necessary for the medical articles to be used in living body and various investigations have been made with respect to such articles for a long time.

However, as well-known, the surface of the shaped articles of the synthetic high polymers, such as polyethylene, polyethylene terephthalate, silicone rubber and the like is non-polar or substantially non-polar and is chemically stable and it has been difficult to coat the surface of said polymer with collagen tightly.

The inventors have made various investigations in order to develop a process by which collagen is coated tightly on the surface of the medical articles composed of synthetic high polymers, such as polyethylene, polyethylene terephthalate, Teflon, silicone rubber and the like and the present invention has been accomplished.

The inventors have attempted such a means that the surface of the shaped articles of synthetic high polymers is firstly treated with known chemical agents, for example, acids, alkalis, chromic acid mixture and phosphorus trichloride or graft polymerized with a reactive different monomer, for example, maleic anhydride, vinyl ether, etc., and then applied with an aqueous solution of collagen and the applied surface is dried and then irradiated with γ-ray, whereby the surface of the shaped article is coated with collagen tightly.

By the above described means, the peel off strength of collagen is 1,000 g/cm for polyethylene, while for silicone rubber, a satisfactory peel off strength is not shown.

The medical articles which are used in direct contact with living body must satisfy the above described requirements and it is not tolerated to contain even a slight amount of impurities. Accordingly, in the above described means, that is, the surface treatment with the chemical agent or the surface graft polymerization, there is a fear of incorporation of impurities and such means are not proper.

Furthermore, in these means the optimum process varies depending upon the synthetic high polymers and these means are troublesome and it is difficult to apply these means in a certain shape of shaped articles and in this point these means are not proper.

The inventors have made experiments systematically with respect to the other means and found that spark discharge is most preferable as the surface treatment and further made investigations with respect to an irradiation of radioactive rays, such as γ-ray, etc., as a means for forming a thin film of collagen. As the results, the method of the present invention has been accomplished by combining these means, wherein collagen can be coated tightly on silicone rubber as well as on polyethylene and the method can be applied to the other synthetic high polymers and further there is no fear of incorporation of impurities during the treating steps.

The present invention consists in a method of manufacturing medical articles composed of various synthetic high polymers coated with collagen, in which a surface of shaped articles composed of a synthetic high polymer selected from the group consisting of polyethylene, polypropylene, polyethylene terephthalate, Tef- Ion, and silicone rubber is subjected to a spark discharge, the thus treated surface is coated with an acidic aqueous solution of collagen and then dried at a temperature of lower than the denaturation temperature of collagen and the shaped article coated with collagen is irradiated with radioactive rays, electron beam or ultraviolet ray under an atmosphere having such a humidity that the water content of the coated collagen becomes more than 20% by weight.

A detailed explanation will be made concerning the first step of the spark discharge.

The surfaces of shaped articles, such as film, pipe, tube, fiber, sponge, container and the like, composed of the synthetic high polymer selected from the group consisting of polyethylene, polypropylene, polyethylene terephthalate, Teflon and silicone rubber, are cleansed in a conventional manner and subjected to a spark discharge.

The spark discharge may be effected in air at room temperature and does not need a special atmosphere but the end of discharged spark must be always moved while contacting with the surface to be treated so that the entire surface is uniformly treated.

As the apparatus for spark discharge, use may be made of various discharging apparatus and, for example, Tesla Coil type discharging apparatus is used and the use of the generated spark discharge of a high frequency is convenient. The amount of discharge is controlled by the length of the discharged spark and the discharge time per area of the treated surface and the final point of the discharge treatment is determined by the angle of contact formed by the treated surface and the water drop fallen on the treated surface or the area where a given amount of water drop occupies the treated surface.

The most important point in this step is the spark discharge condition and the inventors have made numerous experiments with respect to the relation of the spark discharge conditions to the discharge effect and found that a simple relation equation is established between the length of spark, discharge time and discharge effect and the optimum spark discharge conditions have been accomplished based on the novel acknowledge.

Namely, the inventors set the length of spark to 1 cm, 2 cm, 3 cm and 4 cm and said sparks were applied to the surface of the shaped articles composed of synthetic high polymers for the same time per unit area and further said sparks were applied to the surface of the shaped articles by varying the discharge time and the wetting degree of water on the treated surface or the variation of infrared spectrum of the treated surface was determined as the indication of the discharge effect. As the results, it has been found that when the length of spark is represented by L cm, the dishcarge time per unit area is represented by T sec/cm² and the discharge effect is represented by E, the following relation equation is approximately established $$E = k.L.T.$$

where k is a constant.

The discharge effect is proportioned to the product of the length of spark and the discharge time per unit area and when the length of spark is 3 cm, the discharge time is preferred to be 3 to 4 sec/cm², when the length of spark is 1 cm, the discharge time is preferred to be 9 to 12 sec/cm² and when the length of spark is 2 cm, the discharge time is preferred to be 4.5 to 6 sec/cm².

From the above described fact, the optimum condition of spark discharge is 9 to 12 cm.sec/cm². In the case of lower than 9 cm.sec/cm², the discharge effect cannot be attained and in the case of more than 12 cm.sec/cm², the effect does not increase and the synthetic high polymer is deteriorated.

FIG. 1 shows the wetting degree (by water) when the surface of film composed of various synthetic high polymers is treated with the spark discharge under the same condition and the ordinate shows the wetting degree and the abscissa shows the discharge time (sec/cm²) in the length of spark of 3 cm. The wetting degree means S/So.

So: the area where 0.05 ml of water drop occupies on the non-treated film surface.

S : the area where 0.05 ml of water drop occupies on the film surface treated with the spark discharge.

From FIG. 1, it can be seen that when the length of spark is 3 cm, the discharge effect reaches the maximum value at the discharge time of about 4 sec/cm² although there is some difference depending upon the kind of material and that even if the discharge more than 4 sec/cm² is made, the increase of the effect cannot be expected.

Then the second step wherein an acidic aqueous solution of collagen is coated on the surface of the shaped articles composed of synthetic high polymer, is mentioned hereinafter. The concentration of the acidic aqueous solution of collagen is not limited but in view of handling, the concentration is preferred to be about 0.05 to 3% by weight. The acidic aqueous solution of collagen is very viscous and it is difficult to produce a high concentration and even if the solution of a high concentration is prepared, it is difficult to apply said solution uniformly on the surface of the shaped articles. On the other hand, when the concentration is too low, the collagen layer coated on the surface by a single coating and drying application is very thin and pin holes are formed and it is necessary to repeat coating and drying several times. Accordingly, an aqueous solution having a concentration of collagen of about 0.05 to 3% is used in view of handling and if necessary, the coating and drying are repeated to control the thickness of collagen layer.

The process for applying an acidic aqueous solution of collagen is a usual coating process and when the form of the shaped article is complicated, said shaped article is dipped in the acidic aqueous solution of collagen. Furthermore, when the form of shaped article is a container or a tube and only the inner surface of the shaped article is to be coated with collagen an acidic aqueous solution of collagen is introduced into the inside of said shaped article and discharged therefrom.

The thus treated shaped article is dried at a temperature lower than the denaturation temperature of collagen (the denaturation temperature of collagen in water varies depending upon the source of collagen but is about 30° to 37°C) to form collagen layer on the surface of the shaped article. The drying process is preferably natural drying at about 30°C or draft drying. The water content of the collagen layer dried by these processes is usually 15 to 18%.

Then the final step, wherein the shaped article composed of a synthetic high polymer coated with collagen layer is irradiated with radioactive rays, electron beam or ultraviolet ray to fix collagen layer, will be explained.

The essential requirement in the irradiation of radioactive rays, electron beam or ultraviolet ray is that the irradiation is effected under such a condition that the water content of the collagen layer is more than 20% by weight.

The inventors have studied the physical properties of collagen layer irradiated with radioactive rays, electron beam or ultraviolet ray systematically and found that when the water content of collagen layer is less than 20% by weight in the irradiation of collagen, the decomposition take place in preference to the cross-linking and the collagen layer is easily dissolved in water, while when the water content of collagen is more than 20% by weight, as the water content increases, the cross-linking proceeds and when the collagen layer is irradiated with such rays under an atmosphere having a humidity of 100% or in water, the decomposed product (degradation products of low molecular weight extracted with water or a diluted acid) is not substantially formed and a cross-linked strong layer is formed.

A part of the experimental results concerning the film prepared from an acidic aqueous solution of collagen is shown.

Figure 4:
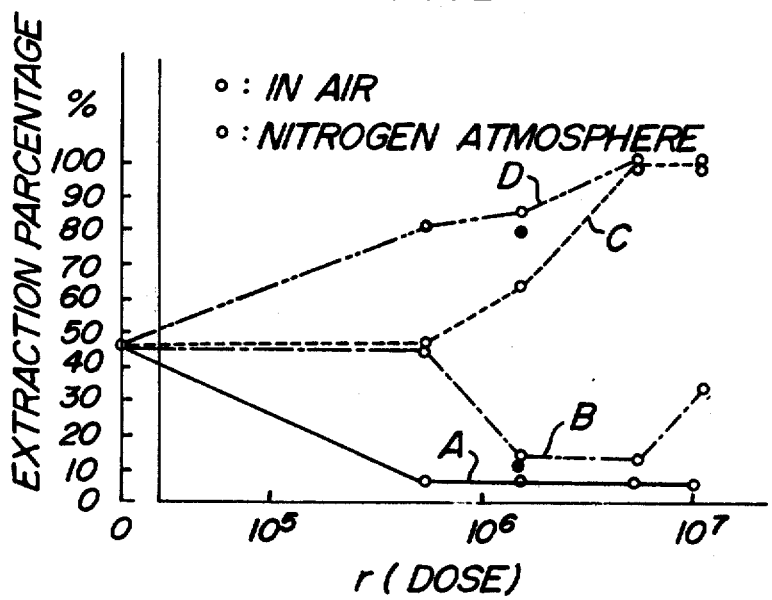
FIG. 4 shows a relation between a dose of γ-ray and an amount of collagen extracted from the collagen film with N/100 HCl aqueous solution at 40°C.
Figure 5:
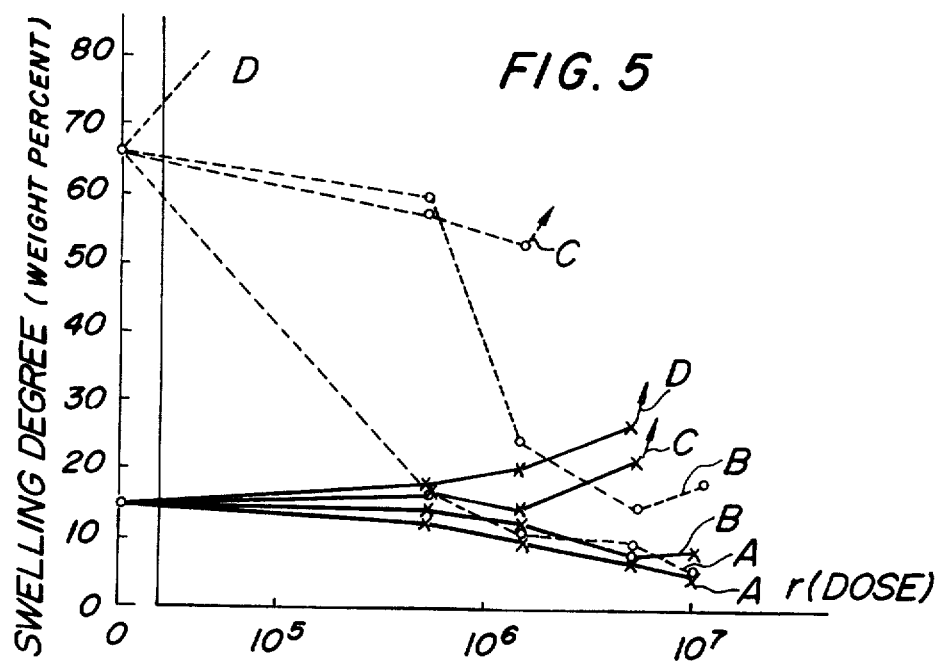

FIG. 5 shows a relation between a dose of γ-ray and the swelling degree of the collagen film with N/100 HCl aqueous solution at 30°C and 40°C. In FIGS. 2 to 5, the experiments were effected in air and nitrogen atmosphere and the curve A shows the irradiation in water (the water content in the collagen film is 80 to 90%), the curve B shows the irradiation under an atmosphere having a humidity of 100% (the water content in the collagen film is 48 to 52.3%), the curve C shows the irradiation under an atmosphere having a humidity of 75% (the water content in the collagen film is 18.2 to 19.2%) and the curve D shows the irradiation under dry atmosphere (the water content of the collagen film is 3.2 to 3.7%). In FIG. 5, the solid line shows the case of 30°C and the broken line shows the case of 40°C.

Figure 1:
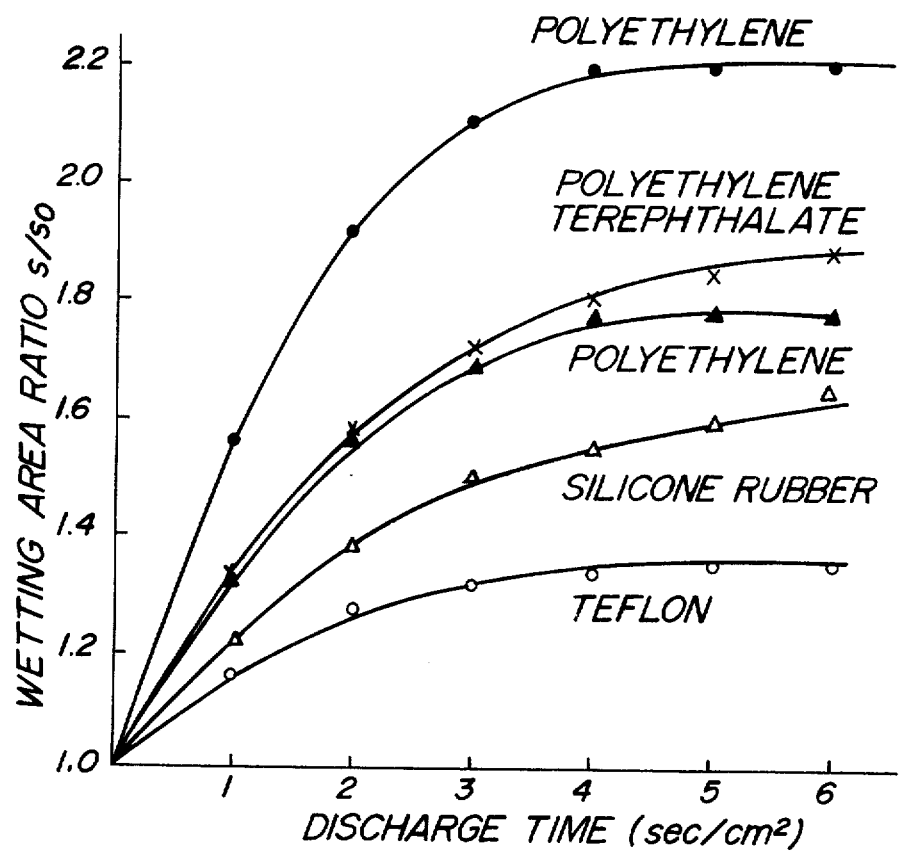
Figure 2:
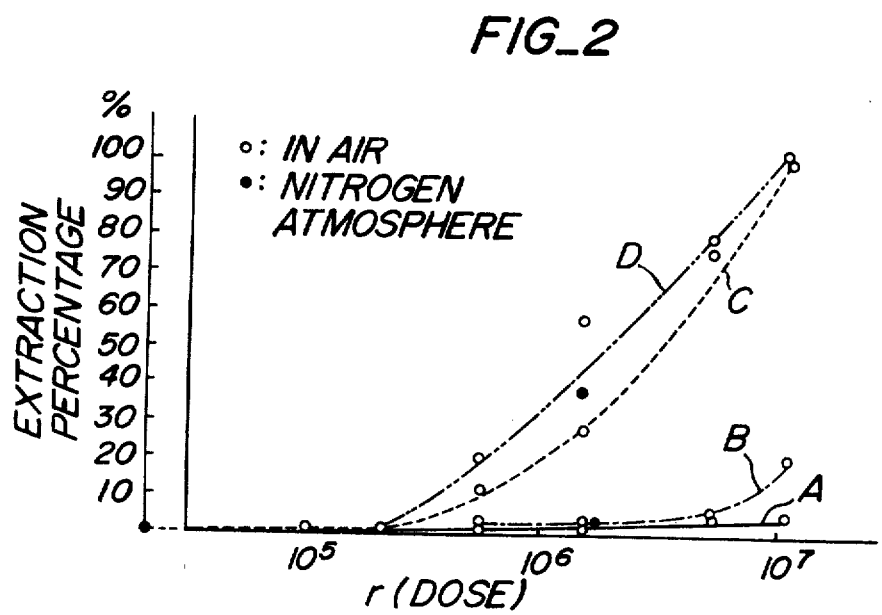
FIG. 2 shows a relation between a dose of γ-ray and an amount of collagen extracted from the collagen film with water at 40°C.

FIG. 2 shows that when the water content of the collagen film is 3.2 to 2.7% in the irradiation with γ-ray, the amount of substance extracted with water (decomposed product of collagen) increases as the dose increases to $10^5r$, $10^6r$ and $10^7r$ and when the dose becomes $10^7r$, 100% of collagen film is dissolved off in water. The collagen film having a water content of 18.2 to 19.2% by weight also increases the substance extracted with water with the increase of the dose of γ-ray. While, in the collagen film having a water content of 48 to 52.3%, the substance extracted with water appears at a dose of $10^7r$ and the collagen film having a water content of 80 to 90% is not extracted with water even at the dose of $10^7r$.

Figure 3:
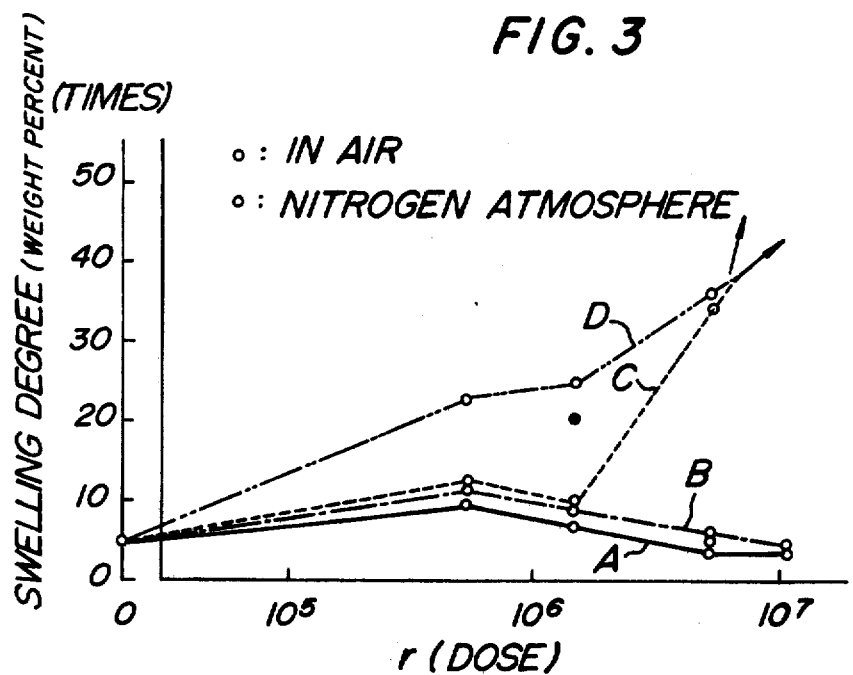
FIG. 3 shows a relation between a dose of γ-ray and the swelling degree of the collagen film with water at 40°C.

FIG. 3 shows that when the collagen film is irradiated with γ-ray, the collagen film having a water content of 3.2 to 3.7% increases the swelling degree of water with the increase of dose of γ-ray and when the dose of γ-ray becomes $10^7r$, all the collagen film is dissolved off as shown in FIG. 2 and the measurement of swelling degree is impossible. This shows that the cross-linking does not occur at all. The collagen film having a water content of 18.2 to 19.2% decreases the swelling degree at the dose of γ-ray of $10^6r$ and this shows the occurrence of cross-linking but when the dose of γ-ray further increases, the swelling degree increases and this shows that the decomposition of collagen prefers to the cross-linking. On the other hand, the collagen film having a water content of 48 to 52.3% decreases the swelling degree even at the dose of γ-ray of $10^7r$ and this shows that the cross-linkage is formed effectively. The collagen film having a water content of 80 to 90% shows the most favorable cross-linkage.

FIGS. 4 and 5 show the case where the experiments were carried out in the same manner as described above by using a dilute hydrochloric acid (N/100 HCl) instead of water and the tendency is the same as in FIGS. 2 and 3.

From the above described fact, it will be understood that their radiation must be performed under an atmosphere having a humidity of more than 75% which makes the water content of collagen layer more than 20%. As well known, hydrophilic high polymers, such as collagen vary the water content depending upon the ambient humidity condition and equilibrate to the atmosphere and in the experiment of the inventors the water content of the collagen film when left to stand in an atmosphere having a humidity of 75% is 18.2 to 19.2% and as the humidity increases, the water content in the collagen film increases.

Then, an explanation will be made with respect to the dose of radioactive rays, electron beam or ultraviolet ray. Concerning the radioactive rays and electron beam, the range of $1-5\times10^6r$ is preferable as shown in FIGS. 2 to 5. If the dose exceeds this range, the decomposition of collagen increases and when the dose does not reach this range, the effect to cross-linking of collagen decreases. Concerning ultraviolet ray, the commercially available ultraviolet ray lamp may be used and the dose is determined by watt number of the ultraviolet ray lamp to be used and the irradiation distance to the material to be irradiated and in general, it is preferred to effect the irradiation with a ultraviolet lamp of 4 watt from a distance of 10 cm for 1.5 hours. Furthermore, it is necessary to adjust the distance of irradiation and time depending upon the watt number of ultraviolet lamp.

By effecting the above described first, second and third steps, it is possible to manufacture silicone rubber coated tightly with collagen, which are used for medical articles to be used in living body.

An explanation will be made with respect to the peel off strength of collagen layer when sheets composed of various synthetic high polymers have been subjected to the above described first, second and third steps.

Figure 6:
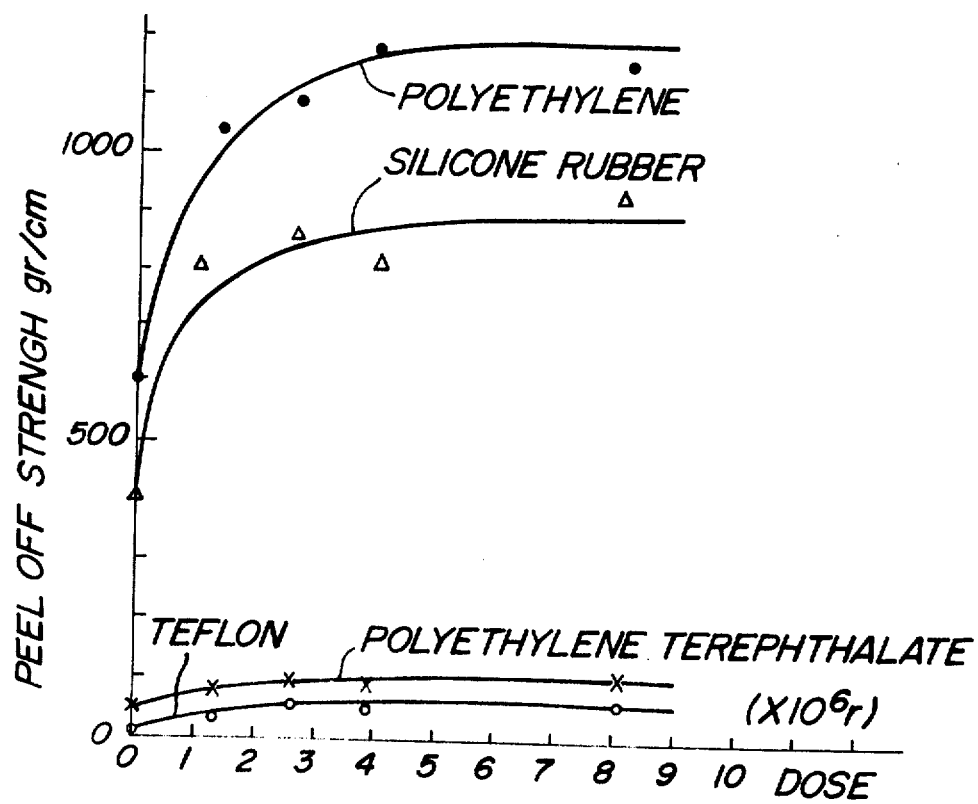

FIG. 6 shows a relation between the dose of irradiation and the peel off strength of collagen layer concerning sheet materials composed of various synthetic high polymers and the ordinate shows the peel off strength and the abscissa shows the dose of γ-ray.

In this case, the surface of the sheet materials is applied to such a discharge treatment that a spark length is 3 cm and a spark discharge time is 3 sec/cm², the thus treated surface is coated with an acidic aqueous solution of collagen, the coated sheet material is dried, the acid is neutralized, the thus treated sheet is washed with water, dried in air and irradiated with γ-ray by varying the dose under nitrogen atmosphere having a humidity of 100% at 20°C.

FIG. 7 shows a relation between the spark discharge time and the peel off strength of collagen layer concerning sheet materials composed of various synthetic high polymers and the ordinate shows the peel off strength and the abscissa shows the discharge time of Tesla discharge of a spark length of 3 cm. FIG. 7 shows the results when the surface of sheet materials composed of various synthetic high polymers is applied to discharge at a given spark length of 3 cm and varying the discharge time, the discharged surface is coated with an acidic aqueous solution of collagen, the coated sheet material is dried, the acid is neutralized, the thus treated sheet is washed with water, the coated surface is dried in air and irradiated with γ-ray at a dose of $1.3 \times 10^6$r (in the case of silicone rubber $1.0 \times 10^6$r) under nitrogen atmosphere having a humidity of 100% at 20°C.

The peel off strength in FIGS. 6 and 7 was determined as follows.

When the peel off load is less than 300 g/cm, an adhesive tape having an adhesive strength of more than 300 g/cm is adhered to the collagen layer coated on the synthetic high polymer sheet material and a load is applied to the tape and the load when the collagen layer is peeled off from the sheet material is read.

When the peel off load is more than 300 g/cm, the collagen layer coated on said sheet material is adhered to a glass plate with silicone adhesive and the load when said sheet material is peeled off from the collagen layer is read.

As seen from FIGS. 6 and 7, the adhesion of the collagen layer to the sheet material which has been treated with the process of the present invention, is very high in the case of polyethylene and silicone rubber, while polyethylene terephthalate and Teflon show a peel off strength of about 50 to 100 g/cm but when these polymeric sheet materials coated with the collagen layer are dipped in water or physiological salt solution for a long time, the collagen is not dissolved off nor peeled off and the practically satisfactory effect can be obtained.

When the artificial blood vessel made of polyethylene terephthalate fibers is coated with collagen by the process of the present invention, collagen penetrates into the space between fibers and coats the fibers and consequently the danger of peeling off is less than the coating of a sheet material.

As mentioned above, in the process of the present invention, a dilute acid, such as hydrochloric acid, acetic acid and the like is used in the acidic aqueous solution of collagen, so that the coated collagen layer contains an acid. Accordingly, it is desirable to neutralize the acid and to remove the resulting salt from the collagen layer. The neutralization and removal of salt may be effected either before or after the third step but a sterilization effect can be attained by the irradiation of radioactive rays in the third step, so that it is preferred to effect the neutralization and removal of salt before the third step, because the resulting product is used in direct contact with living body.

An explanation will be made with respect to the effect attained by the process of the present invention.

As mentioned above, the process of the present invention consists of the first, second and third steps and through each step, (1) the adhesion between collagen and the surface of shaped articles composed of synthetic high polymers increases, (2) the strength increases due to the cross-linking of collagen, (3) the compatibility with living body increases and (4) the sterilization effect can be obtained.

Accordingly, the medical articles to be used in living body, which is composed of synthetic high polymers coated with collagen have a high adhesion between the collagen layer and the surface of the synthetic high polymeric material and have a compatibility with living body, a resistance to coagulation of blood and an affinity to living body and can be used directly without effecting sterilization operation after the manufacture. Furthermore, the process of the present invention consists of technically simple steps and the practice is efficient and economical.

The following examples are given in illustration of this invention and are not intended as limitations thereof. In the example, "%" means "% by weight".

Example 1

After a surface of a silicone rubber sheet as defined hereinbefore (Phycon) was washed with acetone and then with hot water, the sheet was dried in air. A spark discharge having a spark length of 4 cm was applied to the surface in air by means of a spark discharge generator (supply voltage AC 100 V; input current 0.1–0.8 A; frequency 5–100 Kc; spark length 1–5 cm). During the discharge, the end of spark was always moved so as to apply the discharge uniformly as far as possible to the entire surface, and the discharge time was 3 sec/cm². Then, the surface of the sheet was easily wettable.

A 0.5% acidic aqueous solution of collagen (N/400-HCl) was applied on the surface of the above treated sheet, and the sheet was dried in air at 30°C. After dried, the sheet was dipped in a 1% aqueous solution of NH$_4$OH for about 1 hour to neutralize the collagen layer, dipped in cold water 3 times to remove salt, and again dried in air at 30°C.

The sheet was irradiated with γ-rays of $1.0 \times 10^6$ roentgens at 20°C under 100% humidity and gaseous nitrogen atmosphere.

The surface of the resulting silicone rubber sheet was tightly coated with a collagen layer in a thickness of about 6 μ. The collagen layer was not peeled off in a peel off test by means of an adhesive tape. Even after the sheet was dipped in water for 10 days, collagen was not dissolved out in water.

Example 2

After the inner and outer surfaces of a silicone rubber tube (the silicone rubber is the above mentioned Phycon) were cleaned in the same manner as described in Example 1, a metal conductor was placed in the tube and a spark discharge having a spark length of 4 cm was applied to the tube from the outer surface of the tube in air by means of the spark discharge generator used in Example 1. When the end of spark was moved only along the longitudinal direction of the tube during the discharge, the inner and outer surfaces of the tube were discharged with spark. The discharge time was 6 sec/cm². Then, both the inner and the outer surfaces of the tube were easily wettable.

The tube was dipped wholly in a 0.5% acidic aqueous solution of collagen (N/400-HCl), deaired so as not to remain bubbles in the interior of the tube, taken out from the solution and dried in air at 30°C. Since the tube was suspended and dried, the collagen solution applied on he tube fell down dropwise during the drying. The tube was again dipped in the same collagen solution, taken out from the solution and dried at 30°C.

The tube was irradiated with γ-rays in the same manner as described in Example 1.

The surfaces of the resulting silicone rubber tube were tightly coated with a collagen layer in a thickness of about 6 μ. The collagen layers were not peeled off in a peel off test by means of an adhesive tape. Even after the tube was dipped in water for 10 days, collagen was not dissolved out in water.

Example 3

After a surface of a silicone rubber (Phycon) sheet was washed with ethanol and then with hot water, the sheet was dried in air. A spark discharge having a spark length of 3 cm was applied to the surface in air by means of the spark discharge generator used in Example 1. The discharge time was 4 sec/cm². Then, the surface of the sheet was easily wettable.

A 1% acidic aqueous solution of collagen (0.05% $CH_3COOH$) was applied on the surface of the above treated sheet, and the sheet was dried in air at 30°C. After the drying, the sheet was allowed to stand for 1 hour in a gaseous ammonia stream to neutralize the collagen layer, dipped in distilled water for 24 hours to remove salt, and dried at 30°C.

Then, the sheet was irradiated with an electron beam of 1.5 MeV and 100 μA in a dose of $1.2\times10^6$r by means of a van de Graaff electrostatic accelerator under an atmosphere of 90% humidity.

The surface of the resulting silicone rubber sheet was tightly coated with a collagen layer in a thickness of about 10 μ. The collagen layer was not peeled off in a peel off test by means of an adhesive tape. Even after the sheet was dipped in water for 10 days, collagen was not dissolved out in water.

Example 4

The procedure described in Example 3 was repeated, except that an ultraviolet ray was irradiated instead of the electron beam used in Example 3.

That is, the silicone rubber sheet was irradiated with an ultraviolet ray in air at 30°C and under 100% humidity from a distance of 10 cm for 1.5 hour by means of 4 W ultraviolet ray sterilization lamp having a main peak of spectrum at 2,537 A.

The surface of the resulting silicone rubber sheet was tightly coated with a collagen layer in a thickness of about 10 μ. The collagen layer was not peeled off in a peel off test by means of an adhesive tape. Even after the sheet was dipped in water for 10 days, collagen was not dissolved out in water.

What is claimed is:

1. A method of manufacturing medical articles composed of silicone rubber coated with collagen and to be used in a living body comprising
   subjecting a surface of shaped articles composed of silicone rubber in an oxygen-containing atmosphere to a spark discharge wherein the product of the spark length in centimeters and the discharge time per square centimeter is in the range of 9 to 12 cm.sec/cm²,
   coating the thus treated surface with an acidic aqueous solution of collagen,
   drying the collagen coated shaped article at a temperature lower than the denaturation temperature of collagen to form a collagen layer, and
   irradiating the shaped article coated with collagen layer with gamma ray or electron beam to a dosage of $1-5\times10^6$r or the equivalent dosage of ultraviolet light under an atmosphere having a humidity such that the water content of the coated collagen becomes greater than 20% by weight, thus fixing the collagen layer.

2. The method as claimed in claim 1, wherein said gamma rays, electron beam or ultraviolet ray is irradiated under an atmosphere having a humidity of more than 75%.

3. The method as claimed in claim 1, wherein said gamma rays, electron beam or ultraviolet ray is irradiated in water.

4. The method as claimed in claim 1, wherein said shaped article is a film, pipe, tube, fiber, sponge or container.

5. A method of manufacturing medical articles composed of silicone rubber coated with collagen to be used in a living body comprising
   subjecting a surface of a shaped article of film, pipe, tube, fiber or container composed of silicone rubber in an oxygen-containing atmosphere to a spark discharge of 9 to 12 cm.sec/cm² as determined from the spark length in centimeters and the discharge time, per square centimeter,
   coating the thus treated surface with an acidic aqueous solution of collagen,
   drying the collagen coated shaped article at a temperature lower than the denaturation temperature of collagen to form a collagen layer,
   neutralizing the acid in said collagen layer,
   washing the resulting salt with water, and
   irradiating the shaped article coated with collagen layer with gamma rays or electron beam in a dose of $1-5\times10^6$r or the equivalent dosage of ultraviolet light under an atmosphere having a humidity such that the water content of the coated collagen becomes greater than 20% by weight, thus fixing the collagen layer.

* * * * *